United States Patent [19]

Odenwälder et al.

[11] Patent Number: 5,200,306

[45] Date of Patent: * Apr. 6, 1993

[54] COLOR PHOTOGRAPHIC RECORDING MATERIAL CONTAINING A COUPLER WHICH RELEASES A PHOTOGRAPHICALLY ACTIVE COMPOUND

[75] Inventors: Heinrich Odenwälder, Leverkusen; Hans Vetter, Cologne; Peter Bergthaller, Bergisch Gladbach; Dirk Hübner, Cologne, all of Fed. Rep. of Germany

[73] Assignee: Agfa Gevaert Aktiengesellschaft, Leverkusen, Fed. Rep. of Germany

[*] Notice: The portion of the term of this patent subsequent to Jun. 4, 2008 has been disclaimed.

[21] Appl. No.: 674,419

[22] Filed: Mar. 22, 1991

Related U.S. Application Data

[63] Continuation of Ser. No. 447,899, Dec. 8, 1988, abandoned, which is a continuation of Ser. No. 133,637, Dec. 14, 1987, abandoned.

[30] Foreign Application Priority Data

Dec. 24, 1986 [DE] Fed. Rep. of Germany ....... 3644405
Dec. 24, 1986 [DE] Fed. Rep. of Germany ....... 3644416

[51] Int. Cl.$^5$ .............................................. G03C 7/388
[52] U.S. Cl. .................................... 430/505; 430/544; 430/557; 430/558; 430/955; 430/957
[58] Field of Search ............... 430/553, 555, 557, 558, 430/544, 957, 551, 955, 362, 504, 505

[56] References Cited

U.S. PATENT DOCUMENTS 4,049,458 9/1977 Boie et al. ............................ 430/557
5,021,331 6/1991 Vetter et al. ........................ 430/544

Primary Examiner—Lee C. Wright
Attorney, Agent, or Firm—Connolly and Hutz

[57] ABSTRACT

Couplers corresponding to formula I below used in multilayer color photographic recording materials are suitable for the release of photographically active compounds.

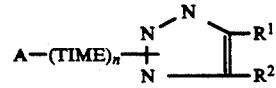

In formula I above,

A represents the residue of a coupler which, as a consequence of a reaction with the oxidation product of a silver halide developer under the photographic development conditions, releases a radical corresponding to the following formula

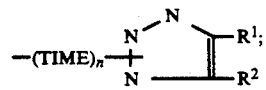

Time represents a bond which, on reaction of the coupler with the oxidation product of a silver halide developer, is released together with the triazole ring attached thereto and, in turn, releases the triazole ring with delay under the development conditions;

n=0, 1 or 2;

$R^1$ and $R^2$ represent any substituents, provided the compound of formula II

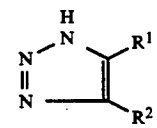

as a whole is a photographically active compound after release.

8 Claims, No Drawings

COLOR PHOTOGRAPHIC RECORDING MATERIAL CONTAINING A COUPLER WHICH RELEASES A PHOTOGRAPHICALLY ACTIVE COMPOUND

This application is a continuation of the copending application Ser. No. 07/447,899 filed Dec. 8, 1988 now abandoned, which is a continuation of the application Ser. No. 07/133,637 filed Dec. 14, 1987, now abandoned, entitled Color Photographic Recording Material Containing A Coupler Which Releases A Photographically Active Compound.

This invention relates to a color photographic recording material comprising at least one photosensitive silver halide emulsion layer containing a coupler which releases a photographically active group, for example a development inhibitor, on color development.

It is known that chromogenic development may be carried out in the presence of compounds which, on development, release substances which are capable of imagewise diffusion and which exhibit a certain effect, for example, are capable of influencing the development of silver halide. If the result of this effect is that further development is inhibited, the compounds in question are called DIR compounds (DIR=development inhibitor releasing). The DIR compounds may be compounds which react with the oxidation product of a color developer with elimination of an inhibitor group to form a dye (DIR couplers) or compounds which release the inhibitor without forming a dye in the process. Such compounds are also called DIR compounds in the narrower sense.

DIR couplers are known, for example, from U.S. Pat. Nos. 3,148,062, 3,227,554, 3,615,506, 3,617,291 and DE-A-2 414 006.

However, the diffusible, photographically active compounds which are released during development may also be, for example, a dye, a coupler, a hardener, a silver halide solvent, a fogging agent, a development accelerator, a developer compound, a bleach inhibitor, a bleach accelerator, a mordant or a sensitizer.

The development inhibitors released are generally heterocyclic mercapto compounds or derivatives of benzotriazole. With regard to the DIR compounds which couple in substantially colorless form, reference is made, for example, to U.S. Pat. No. 3,632,345, DE-A-23 59 295 and DE-A-25 40 959. A number of photographic effects which influence image quality can be obtained by using DIR compounds. Such effects include, for example, the reduction of gradation, the production of a finer color grain, the improvement of sharpness through the so-called edge effect and the improvement of color purity and color brilliance through so-called inter-image effects. In this connection, reference is made, for example, to the article by C. R. Barr, J. R. Thirtle and P. W. Vittum entitled "Development-Inhibitor-Releasing (DIR) Couplers in Color Photography" in Photographic Science and Engineering 13, 74 (1969).

DIR compounds which couple without dye formation have the advantage over DIR couplers which couple with dye formation that they may be universally used so that the same compound may be used in all photosensitive layers of a color photographic recording material irrespective of the color to be produced. By contrast, DIR couplers can generally be used in only some of the photosensitive layers on account of the color produced from them, unless the secondary color density attributable to them is tolerable in the other layers. This advantage of the DIR compounds is offset by the disadvantage that they are generally less reactive than the DIR couplers. In practice, therefore, it is customary to use DIR couplers, if necessary two or more different DIR couplers having to be associated with the differently spectrally sensitized layers according to the color produced from the DIR couplers. Normally, it is important that the photographically active compound be rapidly released from the coupler during development, particularly when the photographically active compound is intended to influence the further course of development. It is thus very desirable for the couplers in question to be highly active. In this connection, particularly significance is attributed to the group of the photographically active compound which is attached to the coupling position of the coupler, the so-called leaving group.

Yellow-forming DIR couplers which include a releasable 3-alkylthio-1,2,4-triazole group are described in DE-A-28 42 063. By using such DIR couplers in a blue sensitive silver halide emulsion layer the color gradation of this layer can be substantially reduced, but the effect on adjacent silver halide layers, in particular on adjacent green and/or red-sensitive silver halide layers is relatively poor. Therefore only slight interimage effects can be brought about by these known DIR couplers.

Further, the yellow-forming DIR couplers of DE-A-34 27 235 which contain a releasable 3-alkylthio-5-furyl-1,2,4-triazole group have satisfying large range efficiency in the sense of interimage effect if used in the blue sensitive layer. They may also be used in greensensitive layers but in this case for producing sufficient interimage effect they have to be used in higher concentrations and therefore cause too high a yellow side density which must be compensated. In red sensitive layers these compounds are nearly ineffective.

Further, in DE-A-26 55 871 there is described a derivative of malonamide carrying in the coupling position a substituted 1,2,4-triazole ring; taken as a DIR coupler the activity of this compound is considerably low.

U.S. Pat. No. 4,049,458 describes various 2-equivalent couplers containing a 1,2,3-triazole ring attached to the coupling position. There is nothing in U.S. Pat. No. 4,049,458 to suggest that this 1,2,3-triazole group develops a certain effect after release; neither was it in fact possible to detect any special effect in these compounds.

The object of the present invention is to provide a color photographic recording material which contains couplers from which the 1,2,3-triazole ring is released as a photographically active compound during development.

The present invention relates to a color photographic recording material comprising at least one photosensitive silver halide emulsion layer and a coupler associated therewith which contains a releasable 1,2,3-triazolyl radical attached to its coupling position, characterized in that the coupler corresponds to the following formula

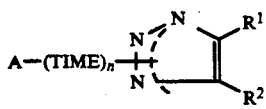

In formula I above,

A represents the residues of a coupler which, as a consequence of a reaction with the oxidation product of a silver halide developer under the photographic development conditions, releases a radical corresponding to the following formula

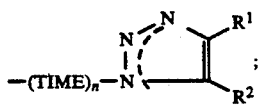

TIME represents a linking group which, on reaction of the coupler with the oxidation product of a silver halide developer, is released together with the triazole ring attached thereto and, in turn, releases the triazole ring with delay under the development conditions;

n=0, 1 or 2;

$R^1$ and $R^2$ represent any substituents not combining to complete a condensed ring, provided the compound of formula II

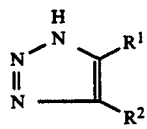

is a whole is a diffusible photographically active compound after release.

In particular the substituents $R^1$ and $R^2$ may have the following meanings according to the invention.

$R^1$ represents H, alkyl, aryl, —S—$R^3$, —O—$R^3$, —CO—$R^3$, a carboxylic acid ester group, an amino group which may be substituted if desired, —CONR$^4$—R$^5$ or a heterocyclic group;

$R^2$ represents halogen, —OH, alkyl, a phenyl group which is substituted with at least one substituent selected from the group consisting of halogen such as F, Cl, Br, I; alkyl such as methyl, ethyl, butyl; aryl such as phenyl; an amino group which may be substituted if desired; alkoxy such as methoxy; aryloxy such as phenoxy; alkylthio such as methylthio; arylthio such as phenylthio; nitro; cyano; —CF$_3$; and acyl such as formyl or acetyl;

naphthyl, —S—$R^3$, —O—$R^3$, —CO—$R^3$, a carboxylic acid ester group having at least 3 carbon atoms, an amino group which may be substituted if desired, —CO—NR$^4$—R$^5$, cyano or a heterocyclic group;

$R^3$ represents alkyl, cycloalkyl, aralkyl, aryl, alkenyl or alkynyl;

$R^4$ represents alkyl, aralkyl, aryl, acyl, —NH$_2$ or acylamino;

$R^5$ represents hydrogen or has the same meaning as $R^4$ or $R^4$ and $R^5$ together represent the balance required to complete a cyclic amino group.

The residue of a coupler represented by A in formula I may be the residue of a coupler which, on color development, produces a cyan, magenta or yellow dye or even the residue of a coupler which produces substantially colorless or only faintly colored products. The coupler residues in question are largely known coupler residues. A large number of colour couplers is known and has been described in numerous Patent Specifications. Reference may be made, for example, to the publications "Farbkuppler" by W. PELZ in "Mitteilungen aus den Forschungslaboratorien der Agfa, Leverkusen/München", Volume III, page 111 (1961) and K. VENKATARAMAN in "The Chemistry of Synthetic Dyes", Vol. 4, 341 to 387, Academic Press, (1971). Cyan couplers generally have a phenolic or naphtholic structure, cf. for example U.S. Pat. Nos. 2,369,929, 2,772,162, EP-A-0 067 689, GB-A-519 208. Magenta couplers are derived from 5-pyrazolone or various pyrazoloazoles, cf. for example DE-A-2 536 191, DE-A-2 703 589 and DE-A-2 813 522, GB-A-1 247 493.

Yellow couplers are derived, for example, from α-acyl acetanilides, such as pivaloyl acetanilides or benzoyl acetanilides, cf. for example U.S. Pat. Nos. 2,875,057, 3,265,506, 4,359,521, DE-A-2 655 871. Couplers which give substantially colorless products and, at the same time, release a photographically active compound are described, for example, in U.S. Pat. Nos. 3,632,345, 3,928,041, 3,958,993, 3,961,959, 4,052,213, 4,088,491.

In a preferred embodiment the coupler of the present invention which releases a photographically useful compound is a DIR coupler of the following formula Ia

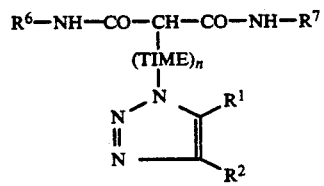

wherein

TIME, n, $R^1$ and $R^2$ have the meaning indicated above;

$R^6$ represents a heterocyclic or carbocyclic aromatic group; and $R^7$ represents alkyl or a residue as defined for $R^6$.

An aromatic group represented by $R^6$ or $R^7$ may be an aryl group such as phenyl or a heterocyclic group such as thiazolyl, benzothiazolyl, thienyl or pyridyl. Said groups may be substituted, for example, with alkyl, alkoxy, halogen, alkoxycarbonyl, carbamoyl, sulfamoyl or acylamino. It is preferred that one or both of the residues $R^6$ and $R^7$ represent phenyl wherein in the latter case said both phenyl groups may be substituted differently.

A linking group represented by TIME in formula I or Ia is a group which, after release from the coupling position of the coupler during its coupling with the oxidation product of the silver halide developer, is capable of releasing a photographically active group attached thereto, in the present case a triazole corresponding to formula II, in a subsequent reaction. The group TIME is also called a timing group because, where such a group is present, the photographically active group thereto is often released and can become active with delay. Known timing groups are, for example, a group

where the O-atom is attached to the coupling position of the coupler while the C-atom is attached to an N-atom of a photographically active compound (for example DE-A-2 703 145), a group which, after release from the coupler, undergoes an intramolecular nucleophilic displacement reaction and, in the process, releases the photographically active compound (for example DE-A-2 855 697), a group in which, after release from the coupler, electron transfer can take place along a conjugated system so that the photographically active compound is released (for example DE-A-3 105 026) or a group

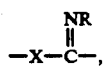

in which X (for example —O—) is attached to the coupling position of the coupler while the C-atom is attached to an atom of the photographically active compound and in which R is an aryl radical for example (for example EP-A-0 127 063).

The group TIME may be present once or even twice in the same or different structuring or (where n=0) may be absent altogether.

An alkyl radical represented by $R^1$, $R^2$, $R^3$, $R^4$ or $R^7$ in formula I or Ia or present in one of these substituents may be linear or branched, substituted or unsubstituted and may contain up to 20 carbon atoms; examples are methyl, ethyl, propyl, isopropyl, butyl, s-butyl, t-butyl, pentyl, hexyl, octyl, dodecyl. The alkyl radicals may be substituted, for example, by hydroxyl, halogen, alkoxy, alkylthio, alkenylthio, acylamino or a cyclic imide group. An alkyl radical represented by $R^1$, $R^2$ or which may be present as a substituent on a phenyl group represented by $R^1$ or $R^2$ preferably contains up to 4 carbon atoms and, more particularly, is a methyl group.

A cycloalkyl radical represented by $R^3$ is for example cyclohexyl; an aralkyl radical ($R^3$, $R^4$) is for example benzyl; and alkenyl radical is for example allyl or 2-butenyl; an alkynyl radical is for example propynyl.

A substituted amino group which may be represented by $R^1$ or $R^2$ is an amino group which is substituted once or twice with (the same or different) substituents selected from the group consisting of alkyl, aralkyl, aryl, amino and acyl, and said substituted amino groups include also cyclic amino groups. A cyclic amino group which may be completed for example by $R^4$ and $R^5$ is for example a piperidino, morpholino, pyrrolidino or pyrrazolyl group.

An acyl radical, which may be contained for example in one of the substituents $R^2$ and $R^4$, such as in an acylamino group is derived from an aliphatic or aromatic carboxylic acid or sulfonic acid or from a carbamic acid or a sulfamic acid or a carbamic acid monoester. An acylamino group represented by $R^1$ or $R^2$ includes for example the following groups; ureido, thioureido, alkoxy carbonylamino and thioacylamino.

A cyclic imido group is, for example, a succinimido group, a maleic imido group, a phthalimido group, a hexahydrophthalimido group or a group corresponding to the following formula

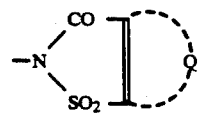

in which Q is the balance required to complete a carbocyclic or heterocyclic, optionally substituted ring.

A heterocyclic group represented by $R^1$ or $R^2$ is, for example, a furyl, thiazolyl or 1,2,4-triazolyl group. A heterocyclic group such as this may contain further substituents, for example alkyl, alkoxy, alkylthio (—S—$R^3$).

The advantageous properties of the couplers according to the invention are presumably attributable to the fact that the 1,2,3-triazole ring not only would appear to be a good leaving group, so that the couplers are highly reactive, but also would appear to show a certain tendency to be adsorbed to the silver halide grain, thus influencing the processes taking place during the development of the silver halide. The groups determining the activity of the photographically active compound would appear to come into particularly good contact with the surface of the silver halide grain. According to the invention, therefore, the photographically active compound is preferably a compound which influences the development of the silver halide, for example a development accelerator, a fogging agent, a bleach accelerator or, more preferably, a development inhibitor. Where the photographically active compound is a development inhibitor, at least one of the radicals $R^1$ and $R^2$ in formulae I and Ia is preferably —S—$R^3$, —COO$R^8$ or a heterocyclic group, $R^3$ representing alkyl with preferably up to 7 carbon atoms, cycloalkyl, aralkyl, alkenyl or alkynyl, and $R^8$ representing a $C_2$-$C_{10}$ alkyl radical or an aryl radical.

It is preferred to use couplers corresponding to one of formulae (III) and (IV) below:

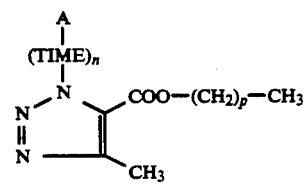

(III)

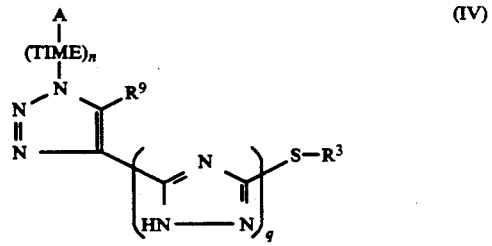

(IV)

in which
TIME has the meaning already defined,
A represents the residue of a cyan coupler, a magenta coupler, a yellow coupler, particularly a yellow coupler which has been derived from malonamide, or a coupler which couples substantially without producing a color;
$R^3$ represents $C_1$-$C_7$ alkyl;
$R^9$ represents H, —CH$_3$, —COO—(CH$_2$)$_p$—CH$_3$;
n=0 or 1;

P is an integer of from 1 to 8;
q=0 or 1.

In formulae (III) and (IV), only one of the several possible isomers in regard to attachment of the triazole ring to the coupling position of the coupler is shown. However, formulae (III) and (IV) are intended to apply equally to the other isomers (not shown here).

Examples of photographically useful compounds according to the invention particularly of development inhibitors are given in the following:

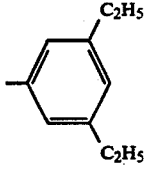

| INH- | R | |
|---|---|---|
| 1 | —(CH$_2$)$_p$—CH$_3$ | p = 3 |
| 2 | —(CH$_2$)$_p$—CH$_3$ | p = 4 |
| 3 | —(CH$_2$)$_p$—CH$_3$ | p = 5 |
| 4 | —(CH$_2$)$_p$—CH$_3$ | p = 6 |
| 5 | —(CH$_2$)$_p$—CH$_3$ | p = 7 |
| 6 | —(CH$_2$)$_p$—CH$_3$ | p = 8 |
| 7 | —CH$_2$—C(CH$_3$)$_3$ | |
| 8 | 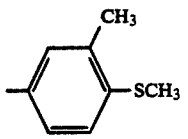 | |
| 9 | 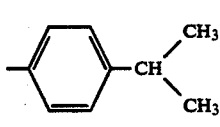 | |
| 10 | —CH$_2$—CF$_2$—CF$_2$—CF$_3$ | |
| 11 | —(CH$_2$)$_2$—S—C$_4$H$_9$ | |
| 12 | —(CH$_2$)$_2$—S—CH$_2$—CH=CH$_2$ | |
| 13 | 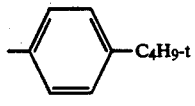 | |
| 14 | —(CH$_2$)$_2$—S—C$_2$H$_5$ | |
| 15 | 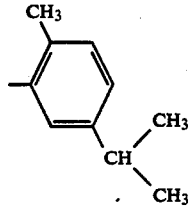 | |
| 16 | —(CH$_2$)$_3$—S—C$_2$H$_5$ | |
| 17 | —(CH$_2$)$_3$—S—C$_3$H$_7$ | |
| 18 | —(CH$_2$)$_3$—S—C$_4$H$_9$ | |
| 19 | 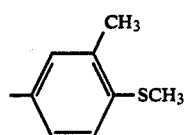 | |
| 20 | 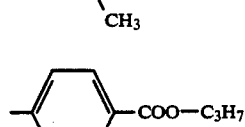 | |
| 21 | 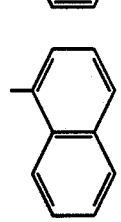 | |
| 22 | 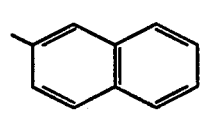 | |
| 23 | 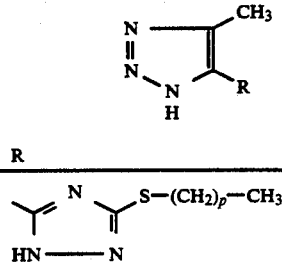 | |
| 24 | 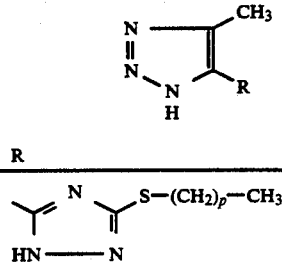 | |
| 25 | 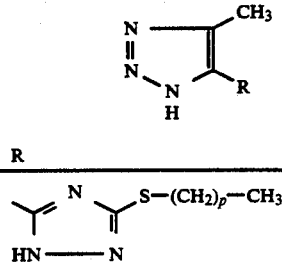 | |
| 26 | 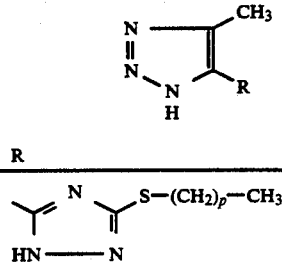 | |
| 27 | 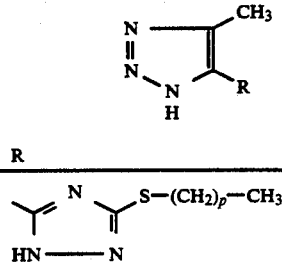 | |
| 28 | 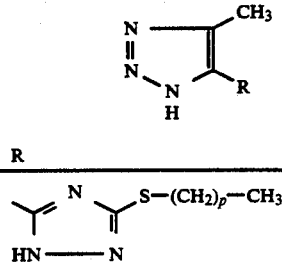 | |

| INH- | R | |
|---|---|---|
| 29 |  | p = 4 |

-continued
| | | |
|---|---|---|
| 30 | 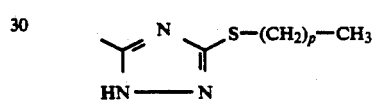 | p = 5 |
| 31 | 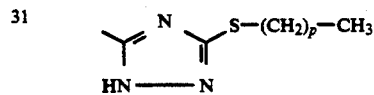 | p = 6 |
| 32 | 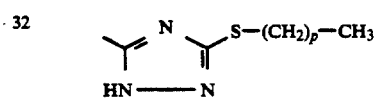 | p = 7 |
| INH-33 | 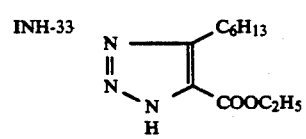 | |
| INH-34 | 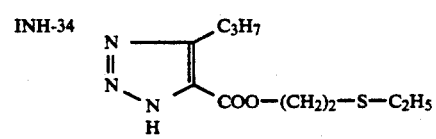 | |
| INH-35 | 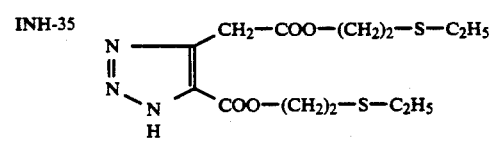 | |
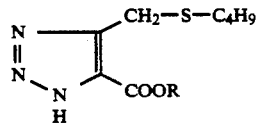
| INH- | R |
|---|---|
| 36 | —$C_2H_5$ |
| 37 | <img phenyl> |
| 38 | <img p-tolyl> |
| 39 | <img naphthyl> |
INH-40 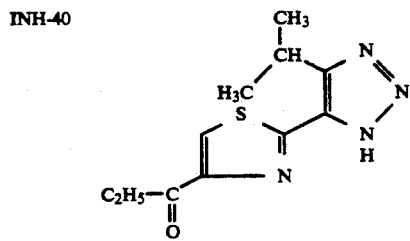
-continued
INH-41 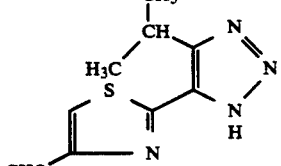
INH-42 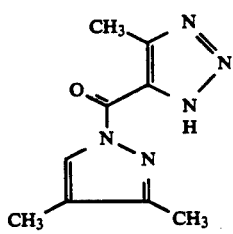
INH-43 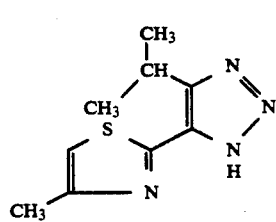
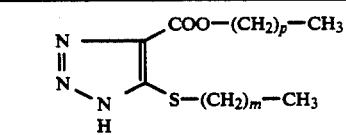
| INH- | p | m |
|---|---|---|
| 44 | 0 | 5 |
| 45 | 0 | 6 |
| 46 | 1 | 4 |
| 47 | 1 | 5 |
| 48 | 4 | 1 |
| 49 | 5 | 1 |
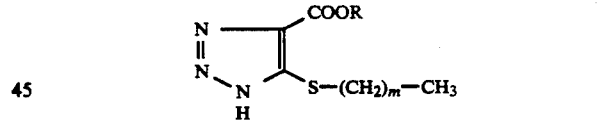
| INH- | R | m |
|---|---|---|
| 50 | <img phenyl> | 2 |
| 51 | <img phenyl> | 3 |
| 52 | <img p-tolyl> | 2 |
| 53 | <img p-tolyl> | 3 |

-continued
| | | |
|---|---|---|
| 54 | 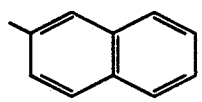 | 2 |
| 55 | 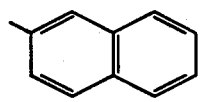 | 3 |
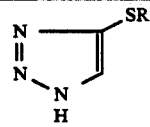
| INH- | R |
|---|---|
| 56 | —C$_4$H$_9$ |
| 57 | —C$_5$H$_{11}$ |
| 58 | 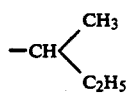 |
| 59 | 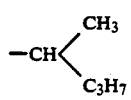 |

| INH- | R |
|---|---|
| 60 | 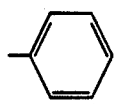 |
-continued
| | |
|---|---|
| 61 | 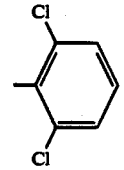 |
| 62 | 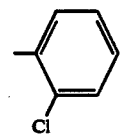 |
| 63 | —S—C$_4$H$_9$ |
| 64 | 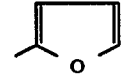 |
| INH-65 | 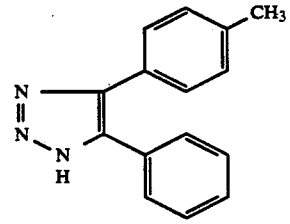 |
| INH-66 | 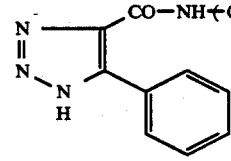 |
| INH-67 | 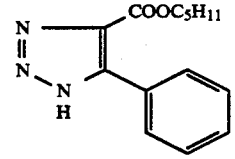 |
Examples of couplers according to the invention are given in the following:
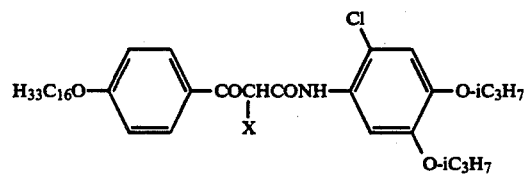
X =
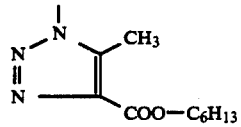
C-1
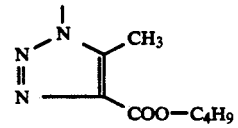
C-2

-continued
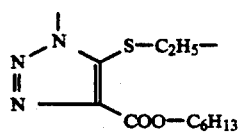 C-3
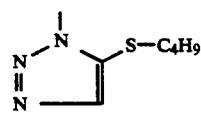 C-4
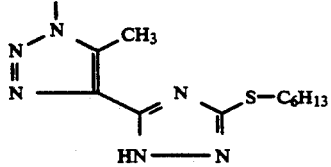 C-5
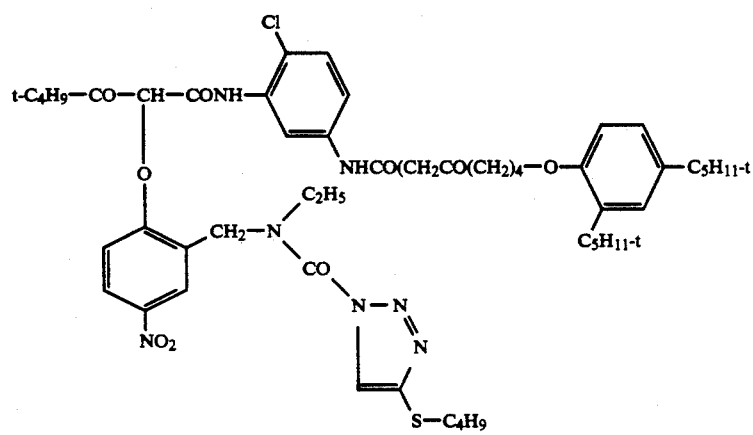 C-6
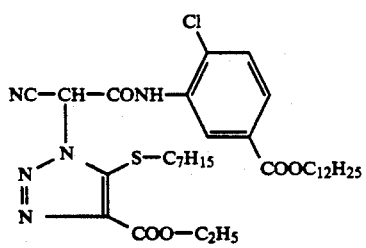 C-7
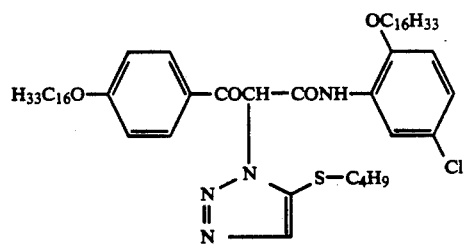 C-8
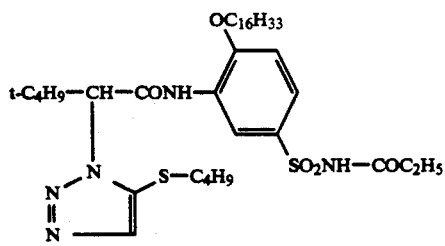 C-9
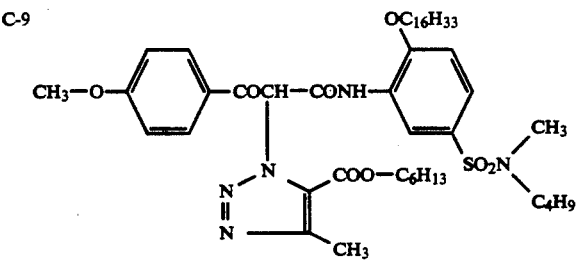 C-10
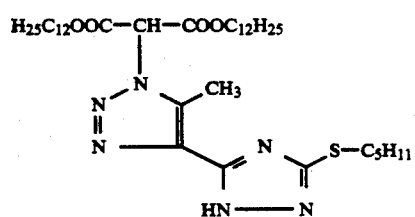 C-11
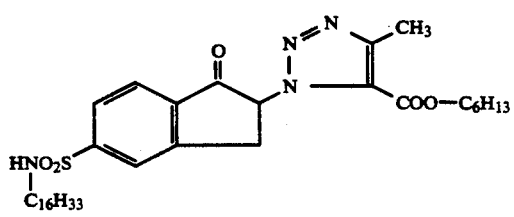 C-12

C-13
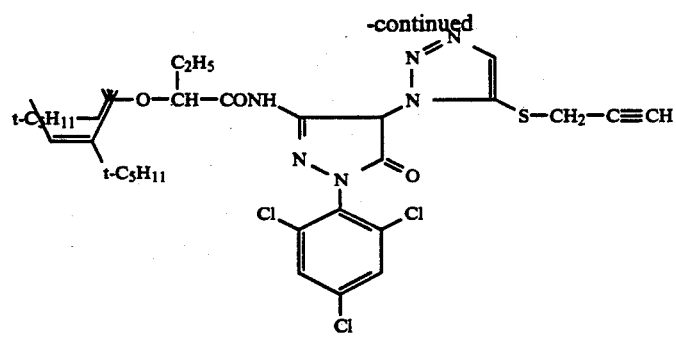
C-14
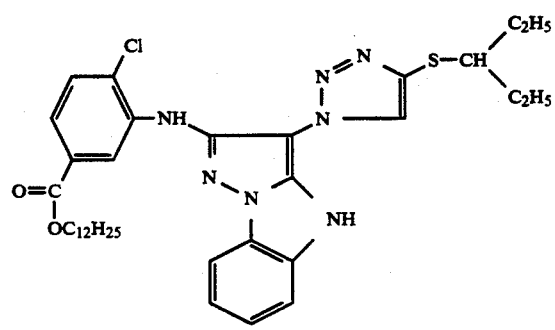
C-15
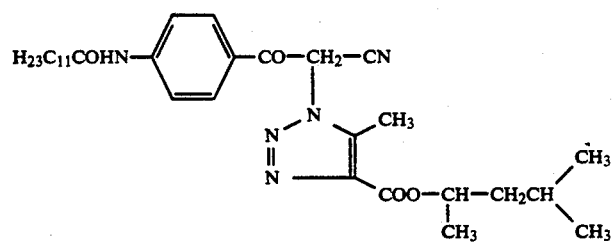
C-16
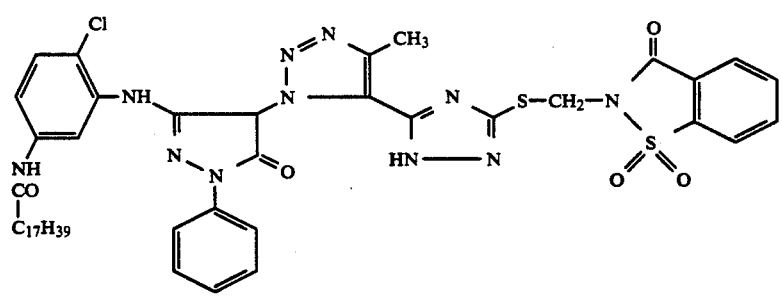
C-17
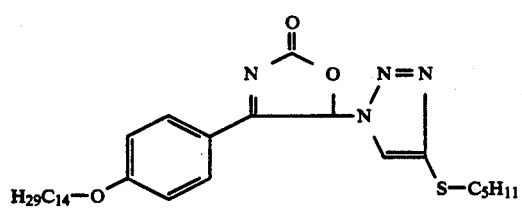
C-18
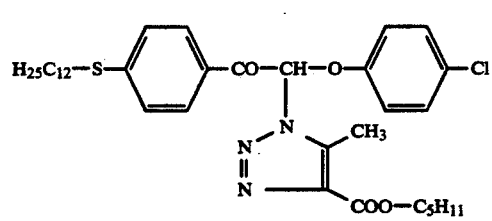
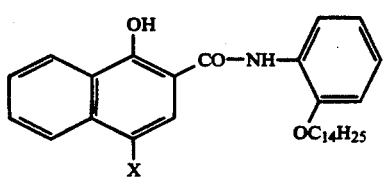

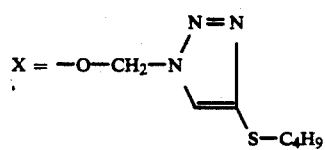
C-19
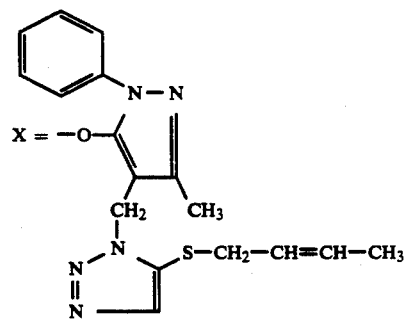
C-20
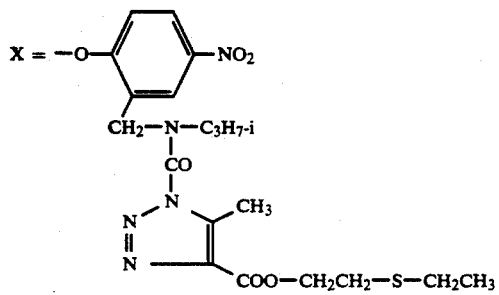
C-21
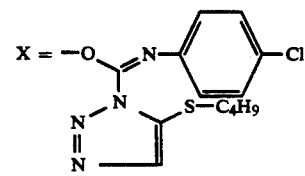
C-22
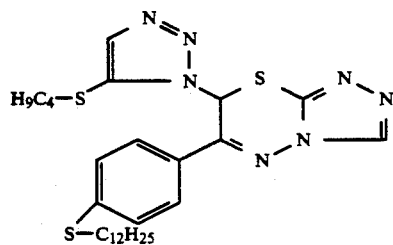
C-23
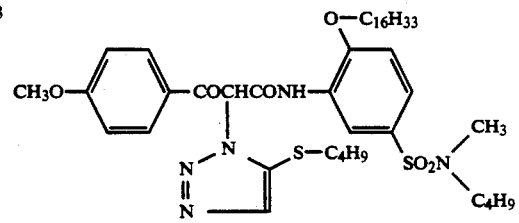
C-24
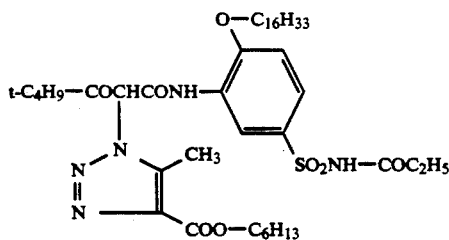
C-25
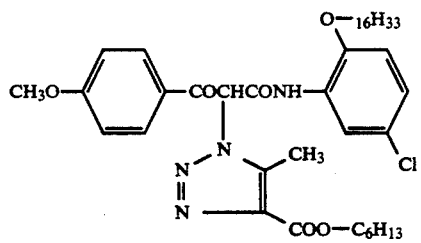
C-26
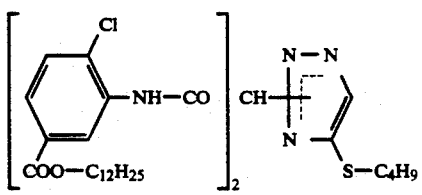
C-27
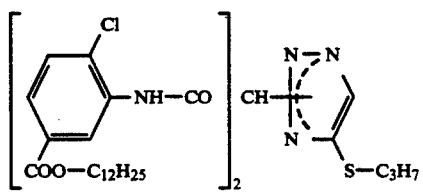
C-28
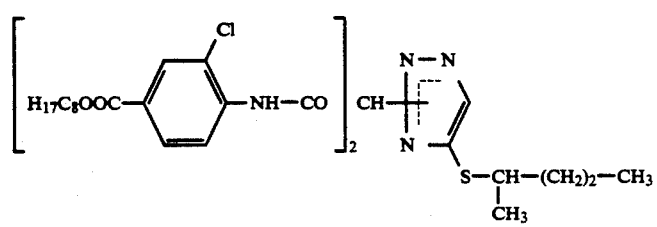
C-29

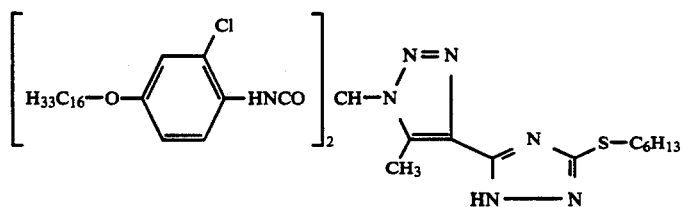
C-30
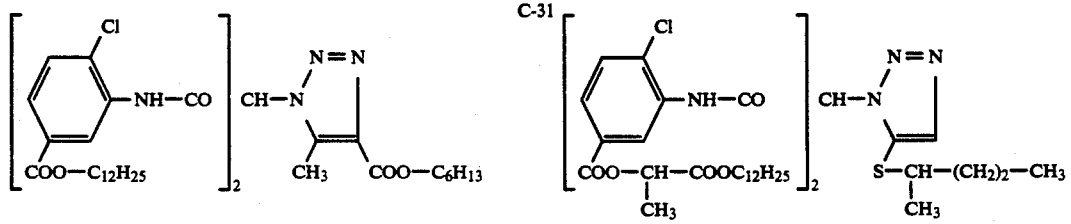
C-31    C-32
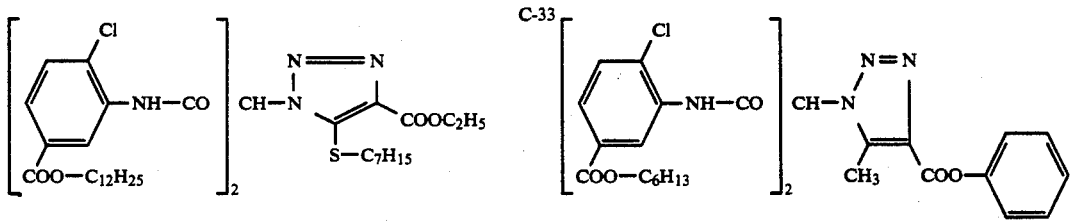
C-33    C-34
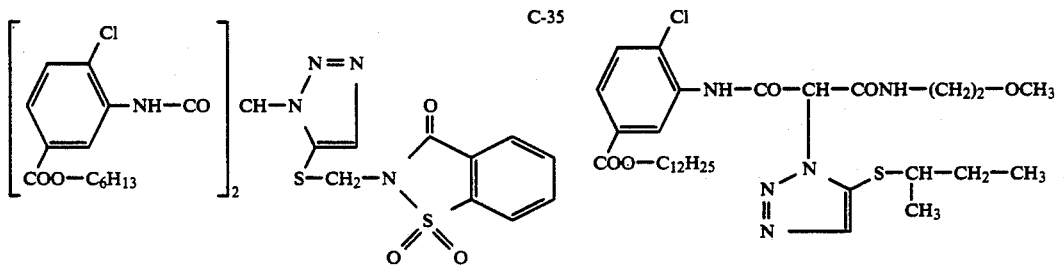
C-35    C-36
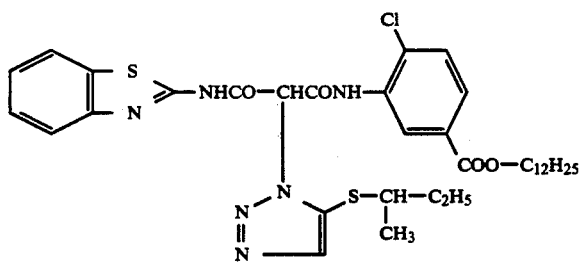
C-37
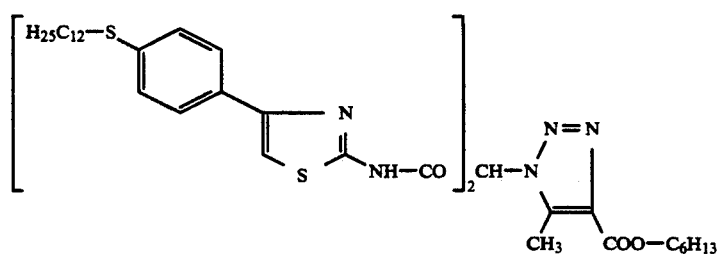
C-38

[Structure C-39: bis-coupler with 2-chloro-5-dodecyloxycarbonyl anilide linked via NH—CO—CH—N to a 1,2,3-triazole bearing S—C₅H₁₁]

[Structure C-40: 2-chloro-5-dodecyloxycarbonyl anilide linked via NH—CO—CH—N to a triazole bearing S—(CH₂)₅—CH₃ and COO—C₂H₅]

In the case of yellow couplers for example, the couplers of formula I according to the invention are readily obtained by condensation of the known α-haloacyl acetanilides corresponding to formula V $$R^{10}-\underset{\underset{Hal}{|}}{CH}-CO-NH-R^7$$

in which
R$^7$ is an aryl radical optionally substituted once or several times;
R$^{10}$ is an acyl radical, for example a benzoyl radical, a pivaloyl radical or a carbamoyl radical;
Hal is a halogen atom, particularly chlorine or bromine,
with triazoles corresponding to formula II.

The reaction is advantageously carried out in an organic solvent, such as dimethylformamide, acetonitrile or acetone, in the presence of a base, such as triethylamine or caustic alkali.

Inhibitors INH-1 to INH-18 were prepared from 4-methyl-1H-1,2,3-triazole-5-carboxylic acid methyl ester (described in Klein et al., J. Heterocyclic Chem. 13, 589 (1976)) by reaction with the corresponding alcohols at 60° to 100° C. in the presence of sodium alcoholate as catalyst. The inhibitors INH-19 to INH-28, INH-37 to INH-39 and INH-50 to INH-55 are prepared by reacting the corresponding triazole carboxylic acid chlorides with the hydroxyaryl compounds in toluene at room temperature with the addition of pyridine.

The compounds INH-29 to INH-32 were prepared by alkylation of the SH compound obtained by Na-alcoholate-catalyzed condensation of 4-methyl-1H-1,2,3-triazole-5-carboxylic acid methyl ester with thiosemicarbazide.

The preparation of 4-(alkyl)-mercapto-1H-1,2,3-triazole-5-carboxylic acid esters which are intermediates for the inhibitors INH-44 to INH-55 is described in Nemerynk et al., Coll. Czech. Chem. Commun. 51, 215 (1981) and Goerdeler et al., Ber. 99, 1618 (1966).

The triazoles INH-56 to INH-59 are prepared for example by alkylation of 5-mercapto-1,2,3-triazole, such as with butyl bromide in the case of inhibitor INH-56.

Since the triazoles corresponding to formula II may occur in various tautomeric forms so that various mesomeric structures may be assigned to the corresponding azeniation, attachment to the carbon atom of the coupling position is possible through various ring nitrogen atoms during the condensation reaction, so that the occurrence of corresponding isomers can be explained. However, this isomerism has no effect upon the performance properties of the DIR couplers according to the invention, so that there is no need for the structure of the possible isomers to be discussed.

The preparation of the couplers according to the invention is described in detail in the following with reference by way of example to the compounds C-2 and C-27.

Preparation of Compound C-2

10 g of the chlorinated coupler

[Structure: CH₃(CH₂)₁₅—O—C₆H₄—CO—CH(Cl)—CO—NH—(2-chloro-4,5-bis(isopropoxy)phenyl)]

and 3 g of 4-methyl-1H-1,2,3-triazole-5-carboxylic acid butyl ester were stirred together with 4.1 g of potassium carbonate in 50 ml of toluene for 15 hours. 7 ml of glacial acetic acid were added, followed by stirring for 1 hour. After the residue had been filtered off under suction, the solution was concentrated. The oil was chromatographed on a silica gel column using a mixture of toluene and ethyl acetate (95:5) and the pure fractions concentrated. The oil thus obtained was stirred overnight in 60 ml of methanol, the crystals filtered off under suction, washed with methanol and dried. Yield 2.5 g of compound C-2 (DIR coupler).

Preparation of Compound C-27

Stage 1: 4-Butylthio-1,2,3-triazole (INH-56)

31.8 g (0.2 moles) of 4-mercapto-1,2,3-triazolesodium salt-dihydrate were dissolved in 200 ml of methanol. 21.7 ml (0.2 moles) of butyl bromide were added and the mixture was refluxed for 2 hours. Then the mixture was poured on ice water and the separating oil was taken up in methylene chloride. The organic phase was washed with water and dried over sodium sulfate. After removal of the solvent the product was chromatographed on a silica gel column using a mixture of toluene and ethylacetate (20:2). A clear oil was obtained.

Yield: 22.8 g (72% of theoretical amount)

Stage 2: Compound C-27

20.7 g (25 mmoles) of α-bromomalonic acid bis-(2-chloro-5-dodecyloxycarbonyl)-anilide were added in portions with stirring at room temperature with 15 minutes to a mixture of 4.27 g (30 mmoles) of the product obtained in stage 1, 5.75 g (50 mmoles) of tetramethylguanidine in 200 ml of ethylacetate. After stirring for an hour the mixture was poured on ice water containing a small amount acetic acid. The organic phase was separated, washed with water, dried and concentrated. The oily residue was stirred up with 20 ml of a mixture of methanol and ethylacetate (3:2). On crystallization the product was collected by filtration. The product obtained was purified by treatment with 200 ml of a mixture of methanol and acetonitrile (1:1) to yield 6.9 g (31% of theoretical amount) of compound C-27; melting point 78°–79° C.

The other compounds according to the invention were similarly prepared, in the case of other coupler parts by already known standard methods.

The compounds according to the invention are suitable for use as couplers in color photographic, more particularly multilayer, recording materials. As yellow couplers, they are preferably used in, or associated with, a photosensitive silver halide emulsion layer predominantly sensitive to the blue spectral region of visible light. The particular advantage of the couplers according to the invention, namely comparatively low inhibition of development in the layer with which such a compound is associated, in addition to comparatively high inhibition of development in adjacent, non-associated layers, is of course of particular relevance when the multilayer color photographic recording material in question is one which, in addition to a predominantly blue-sensitive silver halide emulsion, contains other photosensitive silver halide emulsion layers predominantly sensitive to the green and red spectral regions of visible light. Likewise, as magenta couplers the couplers according to the invention are preferably associated with a green-sensitive layer and, as cyan couplers, with a red-sensitive layer. Couplers which produce little color on development may be associated as required with a blue-sensitive layer, a green-sensitive layer or a red-sensitive layer or even with several of these layers without any danger of color falsification.

Also if they are color couplers, the couplers according to the invention, by virtue of their extremely high activity, may be used in comparatively small quantities to produce the desired effects, particularly the inter-image effects. This makes it possible, for example, to use a yellow DIR coupler according to the invention not only in the blue-sensitive layers producing yellow dye, but also in other layers without an excessive, undesirable secondary density occuring in those layers. Accordingly, the DIR couplers according to the invention as yellow couplers may also be used with advantage in magenta layers and in cyan layers. The same also applies to the magenta couplers and the cyan couplers.

In the production of the photosensitive color photographic recording material, the non-diffusing DIR couplers according to the invention may be incorporated in known manner, optionally together with other couplers, in the casting solution of the silver halide emulsion layers or other colloid layers. For example, oil-soluble or hydrophobic couplers may be added to a hydrophilic colloid solution, preferably from a solution in a suitable coupler solvent (oil former), optionally in the presence of a wetting agent or dispersant. The hydrophilic casting solution may of course contain other standard additives in addition to the binder. The solution of the coupler does not have to be directly dispersed in the casting solution for the silver halide emulsion layer or any other water-permeable layer. Instead, it may even be initially dispersed with advantage in an aqueous non-photosensitive solution of a hydrophilic colloid, after which the mixture obtained is mixed with the casting solution for the photosensitive silver halide emulsion layer or any other water-permeable layer before application, optionally after removal of the low-boiling organic solvent used.

Suitable photosensitive silver halide emulsions are emulsions of silver chloride, silver bromide or mixtures thereof, optionally with a small content of silver iodide of up to 10 mole %, in any of the hydrophilic binders normally used. Gelatin is preferably used as binder for the photographic layers, although it may also be completely or partly replaced by other natural or synthetic binders.

The emulsions may be chemically and spectrally sensitized in the usual way and the emulsion layers and also any other non-photosensitive layers may be hardened in the usual way with known hardening agents.

Color photographic recording materials normally contain at least one silver halide emulsion layer for recording light of each of the three spectral regions red, green and blue. To this end, the photosensitive layers are spectrally sensitized in known manner by suitable sensitizing dyes. Blue-sensitive silver halide emulsion layers need not necessarily contain a spectral sensitizer because, in many cases, the natural sensitivity of the silver halide is sufficient for recording blue light.

Each of the photosensitive layers mentioned may consist of a single layer or, in known manner, for example as in the so-called double layer arrangement, may also comprise two or even more partial silver halide emulsion layers (DE-C-1 121 470). Normally, red-sensitive silver halide emulsion layers are arranged nearer the layer support than green-sensitive silver halide emulsion layers which in turn are arranged nearer than blue-sensitive emulsion layers, a non-photosensitive yellow filter layer generally being arranged between the green-sensitive layers and blue-sensitive layers. However, other arrangements are also possible. A non-photosensitive intermediate layer, which may contain agents to prevent the unwanted diffusion of developer oxidation products, is generally arranged between layers of different spectral sensitivity. Where several silver halide emulsion layers of the same spectral sensitivity are present, they may be arranged immediately adjacent one another or in such a way that a photosensitive layer of different spectral sensitivity is present between them (DE-A-1 958 709, DE-A-2 530 645, DE-A-2 622 922).

Color photographic recording materials for the production of multicolor images by chromogenic development normally contain non-diffusing color couplers for producing the different component dye images cyan, magenta and yellow in spatial and spectral association with the silver halide emulsion layers of different spectral sensitivity.

In the context of the invention, spatial association means that the color coupler is present in such a spatial relationship to the silver halide emulsion layer that the two are capable of interacting in such a way as to allow imagewise accordance between the silver image formed during development and the dye image produced from the color coupler. This result is generally achieved by the fact that the color coupler is contained in the silver halide emulsion layer itself or in an adjacent, optionally non-photosensitive binder layer.

By spectral association is meant that the spectral sensitivity of each of the photosensitive silver halide emulsion layers and the color of the component dye image produced from the particular spatially associated color coupler bear a certain relationship to one another, a component dye image relating to another color (generally for example the colors cyan, magenta or yellow in that order) being associated with each of the spectral sensitivities (red, green, blue).

One or more color couplers may be associated with each of the differently spectrally sensitized silver halide emulsion layers. Where several silver halide emulsion layers of the same spectral sensitivity are present, each of them may contain a color coupler, the color couplers in question not necessarily having to be the same. They are merely required to produce at least substantially the same color during color development, normally a color which is complementary to the color of the light to which the silver halide emulsion layers in question are predominantly sensitive.

In preferred embodiments, therefore, at least one non-diffusing color coupler for producing the cyan component dye image, generally a coupler of the phenol or α-naphthol type, is associated with red-sensitive halide emulsion layers. Advantageous cyan couplers are described, for example, in EP-A-0 028 099, EP-A-0 067 689, EP-A-0 175 573 and EP-A-0 184 057. At least one non-diffusing color coupler for producing the magenta component dye image, normally a color coupler of the 5-pyrazolone, the indazolone or the pyrazoloazole type, is associated with green-sensitive silver halide emulsion layers. Finally, at least one non-diffusing color coupler for producing the yellow component dye image, generally a color coupler containing an open-chain ketomethylene group, is associated with blue-sensitive silver halide emulsion layers. Color couplers of this type are known in large numbers and are described in a number of patent specifications. Reference is made here, for example, to the publications entitled "Farbkuppler (Color Couplers)" by W. PELZ in "Mitteilungen aus den Forschungslaboratorien der Agfa, Leverkusen/München", Vol. III, page 111 (1961) and by K VENKATARAMAN in "The Chemistry of Synthetic Dyes", Vol. 4, 341 to 387, Academic Press (1971).

The color couplers according to the invention may be both typical 4-equivalent couplers and also 2-equivalent couplers in which a smaller quantity of silver halide is required for dye production. 2-equivalent couplers are known to be derived from the 4-equivalent couplers in that they contain in the coupling position a substituent which is eliminated during the coupling reaction. 2-equivalent couplers include both those which are substantially colorless and also those which have a strong color of their own which either disappears during the color coupling reaction or is replaced by the color of the image dye produced. Couplers of the latter type may also be additionally present in the photosensitive silver halide emulsion layers where they serve as masking couplers for compensating the unwanted secondary densities of the image dyes. However, 2-equivalent couplers also include the known white couplers, although couplers such as these do not produce a dye on reaction with color developer oxidation products. 2-equivalent couplers also include the known DIR couplers, i.e. couplers which, in the coupling position, contain a releasable group which is released as a diffusing development inhibitor on reaction with the developer oxidation products. Other photographically active compounds, for example development accelerators or fogging agents, may also be released from such couplers during development.

According to the invention, the color photographic recording material additionally contains at least one 2-equivalent yellow coupler corresponding to formula I which may be present not only in the yellow layer, but also in the magenta layer and/or even in the cyan layer and also in a non-photosensitive layer adjacent one of the layers mentioned.

In addition to the constituents mentioned above, the color photographic recording material according to the invention may contain other additives, such as for example antioxidants, dye stabilizers and agents for influencing the mechanical and electrostatic properties. In order to reduce or avoid the adverse effect of UV light on the dye images produced with the color photographic recording material according to the invention, it is of advantage for example to use UV absorbers in one or more of the layers present in the recording material, preferably in one of the upper layers. Suitable UV absorbers are described, for example, in U.S. Pat. No. 3,253,921, in DE-C-2 036 719 and in EP-A-0 057 160.

The usual layer supports may be used for the materials according to the invention, see Research Disclosure no. 17643, Chapter XVII.

Suitable protective colloids and binders for the layers of the recording material are the usual hydrophilic film-forming agents, for example proteins, more especially gelatin. Casting aids and plasticizers may be used. Reference is made to the compounds mentioned in Research Disclosure no. 17643, Chapters IX, XI and XII.

The layers of the photographic material may be hardened in the usual way, for example with hardeners of the epoxide type, the heterocyclic ethylene imine type and the acryloyl type. The layers may also be hardened by the process according to DE-A-22 18 009 to produce color photographic materials which are suitable for high-temperature processing. It is also possible to harden the photographic layers with hardeners of the diazine, triazine or 1,2-dihydroquinoline series or with hardeners of the vinyl sulfone type. Other suitable hardeners are known from DE-A-24 39 551, DE-A-22 25 230, DE-A-23 17 672 and from the above-cited Research Disclosure 17643, Chapter XI.

Other suitable additives are mentioned in Research Disclosure 17643 and in "Product Licensing Index" December 1971, pages 107 to 110.

To produce color photographic images, the color photographic recording material according to the invention is developed with a color developer compound. Suitable color developer compounds are any developer compounds which are capable of reacting with color couplers in the form of their oxidation product to form azomethine dyes. Suitable developer compounds are aromatic compounds containing at least one primary amino group of the p-phenylenediamine type, for example N,N-dialkyl-p-phenylenediamines, such as N,N-diethyl-p-phenylenediamine, 1-(N-ethyl-N-methylsulfonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine.

Other useful color developers are described, for example, in J. Amer. Chem. Soc. 73, 3100 (1951) and in G. Haist, Modern Photographic Processing, 1979, John Wiley and Sons, New York, pages 545 et seq.

After color development, the material is bleached and fixed in the usual way. Bleaching and fixing may be carried out separately from or even together with one another. Suitable bleaches are any of the usual compounds, for example $Fe^{3+}$ salts and $Fe^{3+}$ complex salts, such as ferricyanides, dichromates, water-soluble cobalt complexes, etc. Particular preference is attributed to iron(III) complexes of amino polycarboxylic acids, more especially for example ethylenediamine tetraacetic acid, N-hydroxyethyl ethylenediamine triacetic acid, alkyliminodicarboxylic acids and of corresponding phosphonic acids. Persulfates are also suitable bleaches.

EXAMPLE 1

A color photographic recording material for negative color development was prepared by applying the following layers in the order indicated to a transparent support of cellulose triacetate. The quantities applied are all based on 1 square meter. For the silver halide applied, the corresponding quantities of $AgNO_3$ are indicated. All the silver halide emulsions were stabilized with 0.5 g of 4-hydroxy-6-methyl-1,3,3a,7-tetra-azaindene per 100 g $AgNO_3$.

Layer 1 (antihalo layer): black colloidal silver sol containing 0.4 g Ag and 3 g gelatin Layer 2 (intermediate layer): 0.5 g gelatin containing 0.05 g of compound SC-1

Layer 3 (1st red-sensitized layer): red-sensitized silver bromide iodide emulsion (5 mole % iodide; average grain diameter 0.50 μm) of 3.5 g $AgNO_3$ containing 1.5 g gelatin, 0.6 g of coupler C-1, 0.06 g of masking coupler MC-1 and DIR coupler according to Table 1

Layer 4 (2nd red-sensitized layer): red-sensitized silver bromide iodide emulsion (10 mole % iodide; average grain diameter 1.5 μm) of 3.7 g $AgNO_3$ containing 1.9 g gelatin and 0.2 g of coupler C-1

Layer 5 (intermediate layer): 0.8 g gelatin containing 0.15 g of compound W-1

Layer 6 (1st green-sensitized layer): green-sensitized silver bromide iodide emulsion (5 mole % iodide; average grain diameter 0.50 μm) of 2.5 g $AgNO_3$ containing 1.4 g gelatin, 0.6 g coupler M-1, 0.07 g masking coupler MC-2 and DIR coupler according to Table 1

Layer 7 (2nd green-sensitized layer): green-sensitized silver bromide iodide emulsion (2 mole % iodide; average grain diameter 1.3 μm) of 2.2 g $AgNO_3$ containing 1.0 g gelatin 0.15 g coupler M-1 0.03 g masking coupler MC-2

Layer 8 (intermediate layer): 0.34 g gelatin containing 0.1 g compound W-1

Layer 9 (yellow filter layer): yellow colloidal silver sol containing 71 mg Ag, 0.5 g gelatin and 0.1 g compound W-1

Layer 10 (1st blue-sensitive layer): silver bromide iodide emulsion (5 mole % iodide; average grain diameter 0.5 μm) of 0.7 g $AgNO_3$ containing 1.4 g gelatin, 0.6 g coupler Y-1 and DIR coupler according to Table 1

Layer 11 (2nd blue-sensitive layer): silver bromide iodide emulsion (10 mole % iodide; average grain diameter 1.5 μm) of 1.5 $AgNO_3$ containing 0.7 g gelatin, 0.15 g coupler Y-1

Layer 12 (intermediate layer): 0.7 g gelatin

Layer 13 (hardening layer): 0.24 g gelatin containing 0.7 g carbamoyl pyridinium salt (CAS Reg. no. 65411-60-1)

The following compounds were used:

Compound SC-1

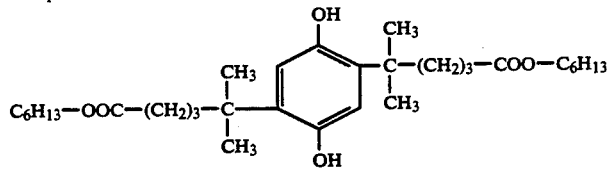

Coupler C-1

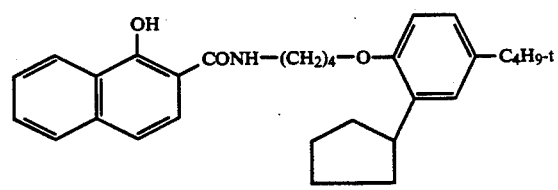

Compound W-1

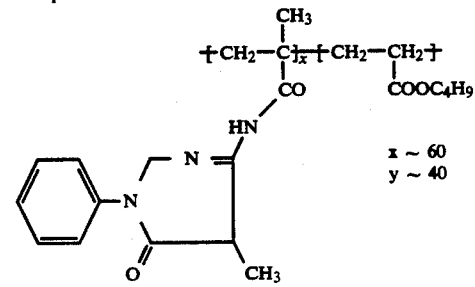

$x \sim 60$
$y \sim 40$

Coupler M-1

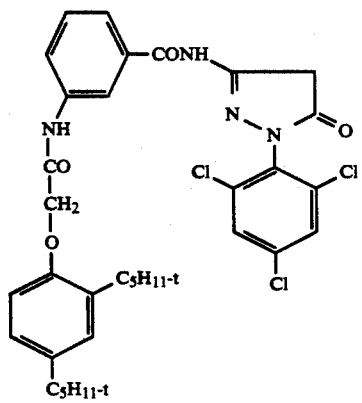
Masking coupler MC-1
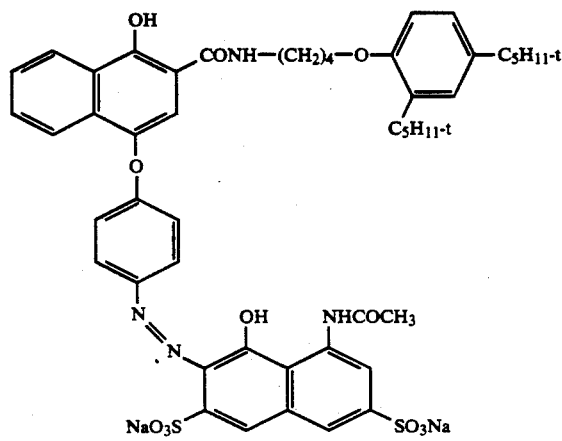
Masking coupler MC-2
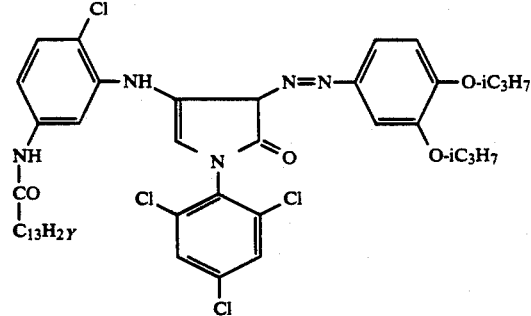
Coupler Y-1
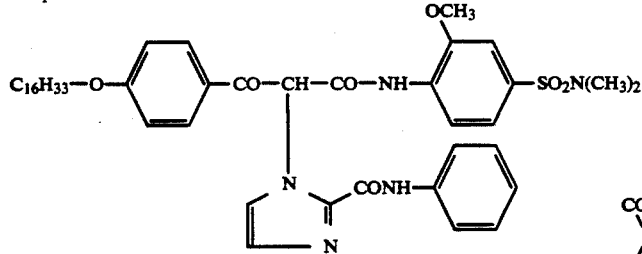
DIR coupler A
-continued
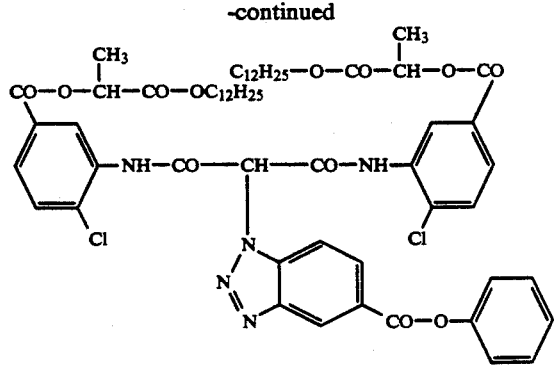

DIR coupler A is described as compound no. 51 in DE-A-32 09 486.

DIR coupler B

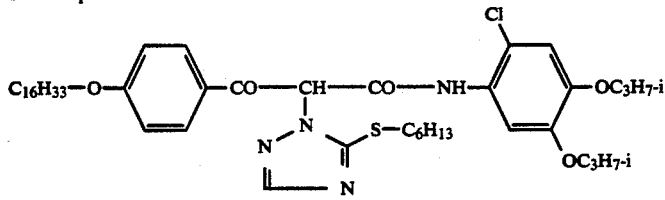

DIR coupler B is described as compound no. 3 in German Patent Application P 36 26 219.6.

DIR coupler C

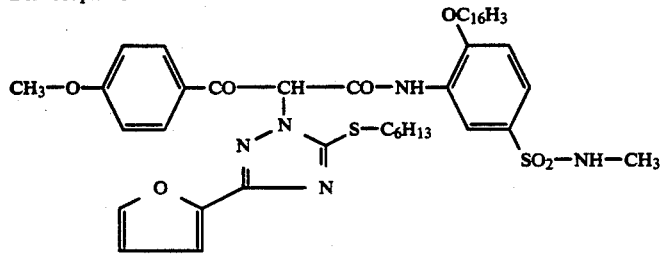

DIR coupler C is described as compound no. 4 in DE-A-34 27 235.

The compounds C-1, M-1, MC-1, MC-2, Y-1 as well as the DIR couplers were used in the form of dispersions, 1 part of gelatin, 2 parts of tricresyl phosphate where compounds M-1 and MC-2 were used, but 2 parts of di-n-butylphthalate in every other case, and 0.1 part of the Na salt of triisopropyl naphthalene sulfonic acid as wetting agent being used to 1 part of the compound used.

Various versions (materials 1 to 6) of the recording material having the described structure were prepared, differing from one another solely in the DIR couplers used in layers 3, 6 and 10. Development was carried out after exposure behind a grey wedge, as described in "The Journal of Photography", 1974, pages 597 and 598.

The results obtained after processing are shown in Table 1. The inter-image effects IIE are calculated as follows:

$$IIE_{cy} = \frac{\gamma_{red} - \gamma_w}{\gamma_w} \; ; \; IIE_{mg} = \frac{\gamma_{green} - \gamma_w}{\gamma_w}$$

where:

$\gamma_{red}$ = gradation on selective exposure to red light
$\gamma_{green}$ = gradation on selective exposure to green light
$\gamma_w$ = gradation on exposure to white light The edge effect EE shown in Table 1 is the difference between micro and macro density for a macro density of 1, as described in James, The Theory of the Photographic Process, 5th Edition, Macmillan Publishing Co, Inc., 1977, page 611:
$EE_{cy}$ = EE in the red-sensitized layer
$EE_{mg}$ = EE in the green-sensitized layer

TABLE 1

| Material | DIR-coupler layer 3 | DIR-coupler layer 6 | DIR-coupler layer 10 | $IIE_{cy}$ | $IIE_{mg}$ | $EE_{cy}$ | $EE_{mg}$ |
|---|---|---|---|---|---|---|---|
| 1 | $3,5 \cdot 10^{-5}$ mole A | $1,8 \cdot 10^{-5}$ mole A | $5,1 \cdot 10^{-4}$ mole C | 45 | 55 | 0,37 | 0,27 |
| 2 | $5,1 \cdot 10^{-5}$ mole B | $4,6 \cdot 10^{-5}$ mole B | $5,1 \cdot 10^{-4}$ mole C | 60 | 55 | 0,46 | 0,35 |
| 3 | $5,1 \cdot 10^{-5}$ mole C-10 | $4,6 \cdot 10^{-5}$ mole B | $5,1 \cdot 10^{-4}$ mole C | 70 | 50 | 0,51 | 0,36 |
| 4 | $5,1 \cdot 10^{-5}$ mole C-22 | $4,6 \cdot 10^{-5}$ mole B | $5,1 \cdot 10^{-4}$ mole C | 60 | 65 | 0,49 | 0,42 |
| 5 | $5,1 \cdot 10^{-5}$ mole C-24 | " | " | 45 | 60 | 0,42 | 0,35 |
| 6 | $5,1 \cdot 10^{-5}$ mole C-9 | " | " | 45 | 60 | 0,43 | 0,40 |
| 7 | $5,1 \cdot 10^{-5}$ mole C-25 | " | " | 45 | 55 | 0,48 | 0,37 |
| 8 | $5,1 \cdot 10^{-5}$ mole C-26 | " | " | 80 | 70 | 0,57 | 0,36 |
| 9 | $5,1 \cdot 10^{-5}$ mole C-27 | $4,6 \cdot 10^{-5}$ mole C-27 | $5,1 \cdot 10^{-4}$ mole K-27 | 65 | 75 | 0,61 | 0,50 |
| 10 | $5,1 \cdot 10^{-5}$ mole C-26 | $4,6 \cdot 10^{-5}$ mole C-31 | $5,1 \cdot 10^{-4}$ mole C | 75 | 45 | 0,65 | 0,45 |
| 11 | $5,1 \cdot 10^{-5}$ mole C-39 | $4,6 \cdot 10^{-5}$ mole C-39 | $5,1 \cdot 10^{-4}$ mole C | 96 | 83 | 0,76 | 0,53 |
| 12 | $5,1 \cdot 10^{-5}$ mole C-40 | $4,6 \cdot 10^{-5}$ mole B | $5,1 \cdot 10^{-4}$ mole C | 60 | 60 | 0,52 | 0,41 |

Particularly good inter-image effects and edge effects are obtained with DIR couplers according to the invention when they are used in more than one layer. In that case, too, the advantages of the DIR couplers according to the invention over those of the prior art are clearly apparent.

We claim:

1. A color photographic recording material comprising at least one silver halide emulsion layer, and associated therewith, a coupler which contains a releasable 1,2,3-triazolyl radical attached to its coupling position, wherein the coupler corresponds to one of the formula III and IV:

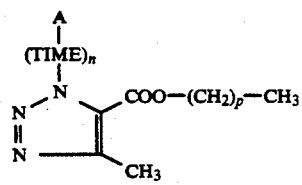

(III)

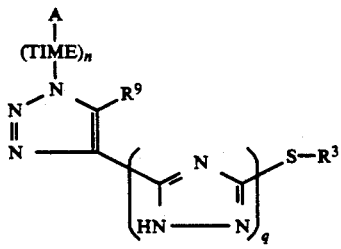

(IV)

A represents the residue of a yellow-forming coupler which coupler is capable of producing a yellow dye upon color development with the oxidation product of a silver halide developer under photographic development conditions;

TIME represents a linking member which, on reaction of a coupler with the oxidation product of a silver halide developer, is released together with the triazole ring attached thereto and, in turn, releases the triazole ring with delay under the development conditions;

$R^3$ is $C_1$-$C_7$ alkyl;

$R^9$ is H, $CH_3$—COO—$(CH_2)_p$—$CH_3$;

n=0 or 1;

p=an integer of from 1 to 8;

q=0 to 1;

said coupler being contained in a predominantly red-sensitive silver halide emulsion layer or a predominantly green-sensitive silver halide emulsion layer.

2. A color photographic recording material comprising a predominantly blue-sensitive silver halide emulsion layer, at least one predominantly green-sensitive silver halide emulsion layer unit with which at least one magenta coupler is associated and a predominantly red-sensitive silver halide emulsion layer unit with which at least one cyan coupler is associated, in which the predominantly blue-sensitive silver halide emulsion layer and at least one partial layer of the predominantly green-sensitive silver halide emulsion layer unit or of the predominantly red-sensitive silver halide emulsion layer unit contain a compound corresponding to one of formulae III and IV:

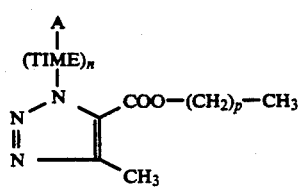

(III)

-continued

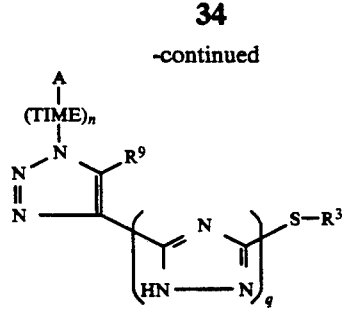

(IV)

wherein

A represents the residue of a yellow-forming coupler which coupler is capable of producing a yellow dye upon color development with the oxidation product of a silver halide developer under photographic development conditions;

TIME represents a linking member which, on reaction of the coupler with the oxidation product of a silver halide developer, is released together with the triazole ring attached thereto and, in turn, releases the triazole ring with delay under the development conditions;

$R^3$ is $C_1$-$C_7$ alkyl;

$R^9$ is H, $CH_3$, —COO—$(CH_2)_p$—$CH_3$;

n=0 or 1;

p=an integer of from 1 to 8;

q=0 or 1.

3. A color photographic recording material comprising at least one photosensitive silver halide emulsion layer and, associated therewith, a coupler which contains a releasable 1,2,3-triazolyl radical attached to its coupling position, wherein the coupler corresponds to the following formula

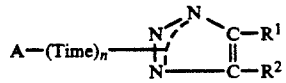

wherein

A represents the residue of yellow coupler which, as a consequence of a reaction with the oxidation product of a silver halide developer under the photographic development conditions, releases a radical corresponding to the following formula

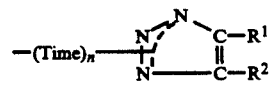

TIME represents a linking group which, on reaction of the coupler with the oxidation product of a silver halide developer, is released together with the triazole ring attached thereto and, in turn, releases the triazole ring with delay under the development conditions;

n=0, 1 or 2;

$R^1$ represents H, alkyl, aryl, —S—$R^3$, —O—$R^3$, —CO—$R^3$, a carboxylic acid ester group, an amino group, —CONR$^4$—$R^5$ or a heterocyclic group;

$R^2$ represents halogen, —OH, alkyl, a phenyl group which is substituted with at least one substituent selected from the group consisting of halogen, alkyl, aryl, an amino group alkocy, aryloxy, alkylthio, arylthio, nitro, cyano, —$CF_3$ and acyl;

naphthyl, —S—$R^3$, —O—$R^3$, —CO—$R^3$, a carboxylic acid ester group having at least 3 carbon atoms, an amino group, —CO—$NR^4$—$R^5$, cyano or a heterocyclic group;

provided that at least one of the substituents $R^1$ and $R^2$ is —S—$R^3$, $COOR^8$ or a heterocyclic group, where $R^8$ is $C_2$-$C_{10}$ alkyl or aryl;

$R^3$ represents alkyl, cycloalkyl, aralkyl, aryl, alkenyl or alkynyl;

$R^4$ represents alkyl, aralkyl, aryl, acyl, —$NH_2$ or acylamino;

$R^5$ represents hydrogen or has the same meaning as $R^4$ or $R^4$ and $R^5$ together represents the residue required to complete a cyclic amino group;

said 1,2,3,-triazolyl radical being attached through a nitrogen atom other than a middle nitrogen, and said coupler being contained in a predominantly red-sensitive silver halide emulsion layer.

4. A recording material as claimed in claim 3, wherein A corresponds to the following formula

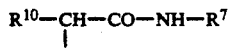

in which
$R^7$ is an aryl radical optionally substituted once or several times;
$R^{10}$ is an acyl radical.

5. A recording material as claimed in claim 4 wherein A corresponds to the following formula:

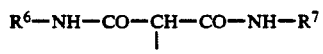

in which
$R^6$ represents a heterocyclic or carbocyclic aromatic group, and
$R^7$ represents alkyl or a group as defined for $R^6$.

6. A color photographic recording material comprising at least one silver halide emulsion layer and, associated therewith, a coupler which contains a releasable 1,2,3,-triazolyl radical attached to its coupling position, wherein the coupler corresponds to the following formula

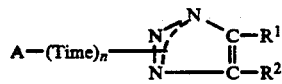

wherein
A represents the residue of a coupler selected from the group consisting of a cyan-forming coupler which is capable of producing a cyan dye upon color development with the oxidation product of a silver halide developer under photographic development conditions,
a magenta-forming coupler which is capable of producing a magenta dye upon color development with the oxidation product of a silver halide developer under photographic development conditions, and
a coupler which is capable of producing a colorless compound upon development with the oxidation product of a silver halide developer under photographic development conditions, and releases a radical corresponding to the following formula

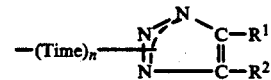

TIME represents a linking group which, on reaction of the coupler with the oxidation product of a silver halide developer is released together with the triazole ring attached thereto and, in turn, releases the triazole ring with delay under the development conditions;

n=0, 1 or 2;

$R^1$ represents H, alkyl, aryl, —S—$R^3$, —O—$R^3$, —CO—$R^3$, a carboxylic acid ester group, an amino group, —$CONR^4$—$R^5$ or a heterocyclic group;

$R^2$ represents halogen, —OH, alkyl, a phenyl group which is substituted with at least one substituent selected from the group consisting of halogen, alkyl, aryl, an amino group, alkoxy, aryloxy, alkylthio, arylthio, nitro, cyano, —$CF_3$ and acyl; naphthyl, —S—$R^3$, —O—$R^3$, —CO—$R^3$, a carboxylic acid ester group having at least 3 carbon atoms, an amino group, —CO—$NR^4$—$R^5$, cyano or a heterocyclic group;

provided that at least one of the substituents $R^1$ and $R^2$ is —S—$R^3$, $COOR^8$ or a heterocyclic group, where $R^8$ is $C_2$-$C_{10}$ alkyl or aryl;

$R^3$ represents alkyl, cycloalkyl, aralkyl, aryl, alkenyl or alkynyl;

$R^4$ represents alkyl, aralkyl, aryl, acyl, —$NH_2$ or acylamino;

$R^5$ represents hydrogen or has the same meaning as $R^4$ or $R^4$ and $R^5$ together represent the residue required to complete a cyclic amino group;

said 1,2,3-triazolyl radical being attached through a nitrogen atom other than a middle nitrogen.

7. A recording material as claimed in claim 6, wherein the coupler corresponds to one of formulae III and IV below:

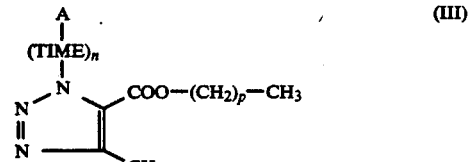

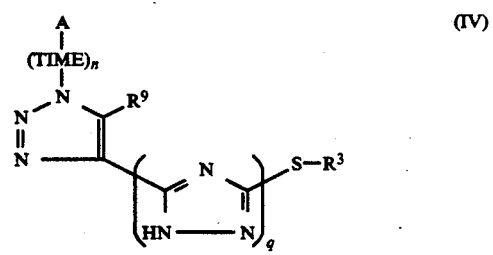

in which
TIME is as defined in claim 6 and
A is the residue of said coupler;
$R^3$ is $C_1$-$C_7$ alkyl;
$R^9$ is H, $CH_3$, —COO—$(CH_2)_p$—$CH_3$;
n=0 or 1;
p=an integer of from 1 to 8;

q=0 or 1.

8. A recording material as claimed in claim 7 including at least one predominantly green-sensitive silver halide emulsion layer unit with which at least one magenta coupler is associated and a predominantly red-sensitive silver halide emulsion layer unit with which at least one cyan coupler is associated, in which at least one partial layer of the predominantly green-sensitive silver halide emulsion layer unit or of the predominantly red-sensitive silver halide emulsion layer unit contains a compound corresponding to one of formulae III and IV.

* * * * *